(12) United States Patent
Toledo-Pereyra et al.

(10) Patent No.: US 7,029,839 B2
(45) Date of Patent: Apr. 18, 2006

(54) METHODS AND SOLUTIONS FOR STORING DONOR ORGANS

(75) Inventors: Luis H. Toledo-Pereyra, Portage, MI (US); Fernando Lopez-Neblina, Vicksburg, MI (US)

(73) Assignee: Human BioSystems, Palo Alto, CA (US)

( * ) Notice: Subject to any disclaimer, the term of this patent is extended or adjusted under 35 U.S.C. 154(b) by 0 days.

(21) Appl. No.: 10/830,863

(22) Filed: Apr. 22, 2004

(65) Prior Publication Data

US 2005/0019917 A1    Jan. 27, 2005

Related U.S. Application Data

(60) Provisional application No. 60/471,028, filed on May 15, 2003, provisional application No. 60/465,114, filed on Apr. 23, 2003.

(51) Int. Cl.
*A01N 1/00* (2006.01)
(52) U.S. Cl. .......................... 435/1.1; 435/1.2; 435/1.3
(58) Field of Classification Search ..................... None
See application file for complete search history.

(56) References Cited

U.S. PATENT DOCUMENTS

| | | | |
|---|---|---|---|
| 2,662,520 A | 12/1953 | McMahon | |
| 2,786,014 A | 3/1957 | Tullis | |
| 3,579,999 A | 5/1971 | Schwartz | |
| 3,729,947 A | 5/1973 | Higuchi | |
| 3,753,357 A | 8/1973 | Schwartz | |
| 3,841,515 A | 10/1974 | Schwartz | |
| 4,059,967 A | 11/1977 | Rowe et al. | |
| 4,473,552 A | 9/1984 | Jost | |
| 4,559,298 A | 12/1985 | Fahy | |
| 4,639,373 A | 1/1987 | Barbior | |
| 4,695,460 A | 9/1987 | Holme | |
| 4,764,463 A | 8/1988 | Mason et al. | |
| RE32,874 E | 2/1989 | Rock et al. | |
| 5,328,821 A * | 7/1994 | Fisher et al. ................. | 435/1.3 |
| 5,474,891 A | 12/1995 | Murphy | |
| 5,487,971 A | 1/1996 | Holme et al. | |
| 5,554,527 A | 9/1996 | Fickensher | |
| 5,622,867 A | 4/1997 | Livesay et al. | |
| 5,635,344 A | 6/1997 | Garcia et al. | |
| 5,827,741 A | 10/1998 | Beattie et al. | |
| 6,080,730 A * | 6/2000 | Lemasters et al. ............ | 514/46 |
| 6,248,363 B1 | 6/2001 | Patel et al. | |
| 6,740,484 B1 * | 5/2004 | Khirabadi et al. ........... | 435/1.3 |

FOREIGN PATENT DOCUMENTS

| | | |
|---|---|---|
| DE | 395432 | 6/1924 |
| DE | 2929278 | 1/1981 |
| EP | 0232672 | 7/1990 |
| FR | 2600671 | 12/1987 |
| GB | 1527655 | 10/1978 |
| JP | 04001135 | 1/1992 |
| SU | 1124974 | 11/1984 |
| WO | WO87/05468 | 9/1987 |
| WO | WO88/01871 | 3/1988 |
| WO | WO91/17655 | 11/1991 |
| WO | WO97/30350 | 8/1997 |
| WO | WO00/53008 A | 9/2000 |

OTHER PUBLICATIONS

Database WPI: Section CH, Week 198524 Derwent Publications Ltd., London, GB AN 1985-144847, XP002130628 & SU1124974A (AS SIBE BIOPHYS).

Broadthagen UA; et al. "Platelet cryopreservation with glycerol, dextran, and mannitol: recovery of 5-hydroxytryptamine uptake and hypotonic stress response" Cryo Biology, (Abstract) Feb. 1985, pp. 1-9, vol. 22.

Smillie JA, et al. "Cryopreservation of human platelets with polyvinylpyrrolidone" Transfusion (Abstract) 1981, pp552-556, vol. 21.

(Continued)

*Primary Examiner*—Sandra E. Saucier
(74) *Attorney, Agent, or Firm*—Wilson Sonsini Goodrich & Rosati (57) ABSTRACT

A method of preserving, storing and transplanting mammalian donor organs. The method includes the cooling of refrigeration preservation, loading pre-freezer preservation, cryopreservation and washing solutions at least containing polyvinylpyrrolidone, a calcium channel blocker, a nucleoside, potassium chloride, polyethylene glycol, at least one amino acid, and a steroid to a temperature of 2° to 4° C. and/or of 0° to 2° C., harvesting a donor organ, perfusing it with one or more of the solution, immersing it in one or more of the solutions and storing it at a temperature above 0° C. or at a temperatures below 0° C. The cryopreservation solution also contains cryopreservative agents. Preserved organs may be transplanted directly from refrigeration storage or from freezer storage by cooling the washing refrigeration preservation solutions to 2° to 4° C., perfusing the organ with washing solution and then preservation solution, and transplanting it.

15 Claims, 7 Drawing Sheets

OTHER PUBLICATIONS

Sputtek A, et al. "Cryopreservation of human platelets with hydroxyethyl starch in a one-step procedure" Cryo Letters (Abstract) 1987, pp218-231, vol. 8.

Odink J; et al. Platelet preservation part 1 the Use of Decrease in Light Absorbance As a screening method in Cryo Preservation studies on Human Platelets , Cryo Biology 1977, pp 519-528, vol. 14 (abstract).

Fern Tablin, "Membrane Phase Transition of Intact Human Platelets: Correlation With Cold-Induced Activation", Journal of Cellular Physiology, 1996, pp305-313, vol. 168.

* cited by examiner

Figure 4 - Solution #1

| Ingredient | Concentration | Range of Concentration |
|---|---|---|
| PEG | 2% | 1-3% |
| Sucrose | 100 mM | 50-200 mM |
| PVP-40 | 1% | 1-3% |
| Verapamil | 10 ml/L | 1-20 ml/L |
| Trimethoprim | 0.5 ml/L | 0.1-1ml/L |
| Adenosine | 5 mM | 1-10 mM |
| MgSO4 | 5 mM | 1-10 mM |
| KCl | 15 mM | 10-20 mM |
| MgCl | 5 mM | 1-10 mM |
| NaCl | 10 mM | 5-15 mM |
| Glycine | 100 mM | 50-150 mM |
| N-acetylcysteine | 10 mM | 10-50 mM |
| Arginine | 10 mM | 10-50 mM |
| Proline | 5 mM | 1-10 mM |
| Glutamine | 5 mM | 1-10 mM |
| Serine | 5 mM | 1-10 mM |
| Pyruvate | 10 mM | 1-10 mM |
| Lidocaine | 2 mM | 1-5 mM |
| Dexamethasone | 10 mg/L | 5-50 mg/L |
| Ethacrynate | 10 mg/L | 10-50 mg/L |

Figure 5 - Solution #2

| Ingredient | Concentration | Range of Concentration |
|---|---|---|
| PEG | 3% | 1-4% |
| Sucrose | 200 mM | 50-200 mM |
| PVP-40 | 1% | 1-3% |
| Verapamil | 10 ml/L | 1-20 ml/L |
| Trimethoprim | 0.5 ml/L | 0.1-1ml/L |
| Adenosine | 5 mM | 1-10 mM |
| MgSO4 | 5 mM | 1-10 mM |
| KCl | 15 mM | 10-20 mM |
| MgCl | 5 mM | 1-10 mM |
| NaCl | 2.5% | 1-5% |
| Glycine | 100 mM | 50-150 mM |
| N-acetylcysteine | 10 mM | 10-50 mM |
| Arginine | 10 mM | 10-50 mM |
| Proline | 5 mM | 1-10 mM |
| Glutamine | 5 mM | 1-10 mM |
| Serine | 5 mM | 1-10 mM |
| Pyruvate | 10 mM | 1-10 mM |
| Lidocaine | 2 mM | 1-5 mM |
| Dexamethasone | 10 mg/L | 5-50 mg/L |
| Ethacrynate | 10 mg/L | 10-50 mg/L |

Figure 6 - Solution #3

| Ingredient | Concentration | Range of Concentration |
|---|---|---|
| PEG | 3% | 1-4% |
| Sucrose | 200 mM | 50-200 mM |
| PVP-40 | 1% | 1-3% |
| Verapamil | 10 ml/L | 1-20 ml/L |
| Trimethoprim | 0.5 ml/L | 0.1-1ml/L |
| Adenosine | 5 mM | 1-10 mM |
| MgSO4 | 5 mM | 1-10 mM |
| KCl | 15 mM | 10-20 mM |
| MgCl | 5 mM | 1-10 mM |
| NaCl | 10 mM | 5-15 mM |
| Glycine | 100 mM | 50-150 mM |
| N-acetylcysteine | 10 mM | 10-50 mM |
| Arginine | 10 mM | 10-50 mM |
| Proline | 5 mM | 1-10 mM |
| Glutamine | 5 mM | 1-10 mM |
| Serine | 5 mM | 1-10 mM |
| Pyruvate | 10 mM | 1-10 mM |
| Lidocaine | 2 mM | 1-5 mM |
| Dexamethasone | 10 mg/L | 5-50 mg/L |
| Ethacrynate | 10 mg/L | 10-50 mg/L |
| Glycerol | 15% (v/v) | 15-30% |
| Propanediol | 15% (v/v) | 5-15% |
| Ethanol | 5% (v/v) | 1-10% |
| Dimethyl sulfoxide | 5% (v/v) | 1-10% |

Figure 7 - Solution #4

| Ingredient | Concentration | Range of Concentration |
|---|---|---|
| PEG | 3% | 1-4% |
| Sucrose | 200 mM | 50-200 mM |
| PVP-40 | 1% | 1-3% |
| Verapamil | 10 ml/L | 1-20 ml/L |
| Trimethoprim | 0.5 ml/L | 0.1-1ml/L |
| Adenosine | 5 mM | 1-10 mM |
| MgSO4 | 5 mM | 1-10 mM |
| KCl | 15 mM | 10-20 mM |
| MgCl | 5 mM | 1-10 mM |
| NaCl | 10 mM | 1-50 mM |
| Glycine | 100 mM | 50-150 mM |
| N-acetylcysteine | 10 mM | 10-50 mM |
| Arginine | 10 mM | 10-50 mM |
| Proline | 5 mM | 1-10 mM |
| Glutamine | 5 mM | 1-10 mM |
| Serine | 5 mM | 1-10 mM |
| Pyruvate | 10 mM | 1-10 mM |
| Lidocaine | 2 mM | 1-5 mM |
| Dexamethasone | 10 mg/L | 5-50 mg/L |
| Ethacrynate | 10 mg/L | 10-50 mg/L |

METHODS AND SOLUTIONS FOR STORING DONOR ORGANS

This application claims the benefit of U.S. Provisional Application No. 60/471,028, filed May 15, 2003, and U.S. Provisional Application No. 60/465,114 filed Apr. 23, 2003, both of which are incorporated herein by reference.

FIELD OF THE INVENTION

The invention relates generally to organ storage systems. More particularly, the invention relates to solutions and methods for preserving donor organs and storing them for extended periods of time before transplantation or other use in the future.

BACKGROUND OF THE INVENTION

One of the greatest problems in donor organ transplantation is the storage and preservation of organs between the time of harvest from a donor and the time of transplantation into a recipient. The amount of time that can lapse between the two events is quite limited because the cells and tissues of the donor organ deteriorate over time, even if they are stored at refrigerated temperatures. Once harvested, cells and tissues are deprived of the oxygen that is required to maintain internal metabolism and cell volume integrity. To counteract the ill effects of low oxygen, standard techniques for modern organ preservation involve the exposure of a harvested organ to preservation solutions at cold temperatures not below 0° C. Although colder temperatures are a solution to oxygen deprivation in donor organ tissue, they present their own problems. Cold or hypothermic conditions may lead to cellular damage including a reduced ability to generate energy, maintain cell volume integrity, and also swelling and/or cell death.

A widely used preservation solution is commonly known as University of Wisconsin (UW) solution or Viaspan, which is manufactured by DuPont. However, the preservation of donor organs using Viaspan is generally limited to a 36-hour period in kidneys before the organs begin to deteriorate. For example, if kidneys are perfused with UW solution and packed on ice, surgeons will attempt to use them within 24 hours but not later than 36 hours after harvesting. A principal problem however is that the viability of the donor kidney decreases over time of storage so that by 36 hours there is at least some damage to the tubular cells. This generally results in decreased viability of the kidney cells so that urine production and proper kidney function are delayed after transplant. As a result, artificial kidney function or dialysis is generally required for full recovery of a recipient after transplantation.

Storage of organs at sub-zero temperatures is not possible or extremely difficult because the tissue and water in the organ usually freezes. These relatively lower temperature ranges cause damage or destruction to the cells and tissues. Today there are some solutions currently available for organ storage purposes such as Viaspan, but their capacity to store organs effectively is generally limited. There is a need for improved solutions and methods for effective organ preservation for extended periods of time.

SUMMARY OF THE INVENTION

The invention describes solutions and methods for preserving donor organs for use in transplantation or other medical purposes in the future. In accordance with one aspect of the invention, a variety of storage methods at different temperatures are provided. The invention provides for example a first series of methods for cold storage or storage at refrigerator temperatures (about 0° to about 6° C.), and a second series of methods for storage at sub-zero temperatures as low as about −20° C., which is generally the equivalent to a refrigerator freezer temperatures, or even lower temperatures including cryopreservation temperatures that drop to as low as about −80° C. Other aspects of the invention provide preservation solutions that can be designed to provide low temperature organ storage benefits including reduction of interstitial edema and endothelial swelling. These solutions can also provide antioxidant and anti-proteolytic protection, can preserve proper intracellular ion concentration, and can offer an energy source to support cellular functions including the Krebs cycle.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Current organ preservation, storage and transplantation procedures are limited because organs are so vulnerable to damage after removal from a donor. Once harvested, cells and tissues are deprived of the oxygen that is required to maintain internal metabolism and cell volume integrity. This low oxygen state is called ischemia and leads to hypoxia, which prevents oxygen from being delivered to the organ tissue. Without oxygen, cellular tissue can suffer injury as cell metabolism fail and individual cells can be subject to swelling or inflammation.

To counteract the ill effects of ischemia, standard techniques for modern organ preservation involve the exposure of a harvested organ to preservation solutions at cold temperatures not below 0° C. This treatment essentially creates hypothermic conditions that reduce a cell's need for metabolic oxygen. Components of the solution and the cold environment combine to protect the cell from ischemic conditions and thereby prevent the onset of injury. This procedure is known as cold flush preservation, in which the preservation solutions are designed to eliminate chemical potential gradients across the cell membranes of the cells composing the organ. By doing so the solution tends to mimic the intracellular environment and prevent the donor organ cells from activating metabolic pathways. Although hypothermia is a solution to oxygen deprivation in donor organ tissue, it presents its own problems. The cells of an organ preserved under hypothermic conditions lose their ability to source of ATP, and therefore cannot produce the energy required to regulate the sodium-potassium pump, which is one of the most important modulators of internal cell volume. Also the hypoxic environment induces the release of intracellular calcium and elevated concentrations of calcium can lead to subsequent activation of multiple metabolic inflammatory pathways. As a result, the cells may exhibit endothelial cell swelling, a loss of blood vessel integrity, including the reduction in the internal diameter of blood vessels called a vasospasm, and even cell death in tubules.

One of the most widely used solutions in organ preservation and storage is known as University of Wisconsin (UW) solution or Viaspan, which is manufactured by DuPont. However, preservation of donor organs using Viaspan is generally limited to a 36-hour period in kidneys before the organs begin to deteriorate.

In general, the current limitations on donor organ preservation time seriously hamper the capacity of organ transplantation procedures. The 36-hour time frame allowed for kidneys does not always provide sufficient time for accurate cross-matching of donors and recipients, which is needed to increase the chances of a successful transplant. In addition, the time required for transnational and trans-international transport of donor organs and of recipients may exceed the viability period of organs preserved under current procedures.

Methods for Preservation, Storage and Transplantation

The invention provides improved methods and solutions for storing organs for future medical uses such as organ transplants into a recipient. In one aspect of the invention, methods are provided using various preservation solutions and cryopreservation solutions to prepare and store a donor organ after it is harvested. The preserved organ can then be placed in storage at an appropriate temperature for prolonged periods of time that can be greater than 36 hours. With respect to another embodiment of the invention, when the preserved organ is required for transplantation, the combination of a preservation solution and a washing solution can be utilized to thaw the organ from storage and transplant it into a recipient.

Figure 1:
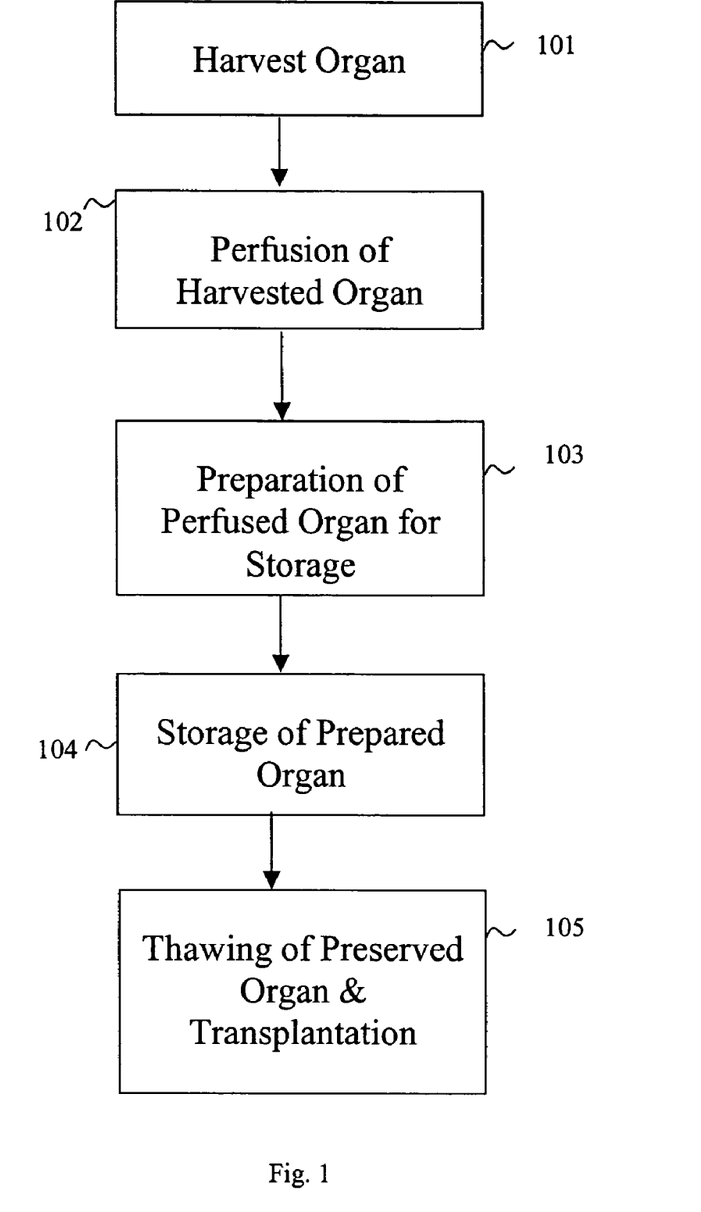
FIG. 1 is an overall flowchart illustrating the operation of an embodiment of the invention that provides methods for organ preservation and transplantation.

FIG. 1 is an overall flowchart illustrating the operation of one embodiment of the invention that provides organ preservation and transplantation methods. At step 101, a mammalian organ is removed or harvested from a donor. It may be a liver, kidney, pancreas, heart or any other type of mammalian organ or tissue. Step 102 represents the application of a preservation solution on to a harvested donor organ. In another embodiment of the invention, it may be preferable to have the solution perfused through the donor organ. In step 103, the donor organ is prepared for storage at an appropriate temperature. The donor organ can also be maintained in the preservation solution and placed in storage. This aspect of the invention provides for the application, perfusion, infusion or immersion of the donor organ into a cryopreservation solution before storing the donor organ at an appropriate temperature.

At the time a donor organ becomes available, a potential recipient may not yet have been identified. One embodiment of the invention addresses such a problem as follows. The donor organ may be prepared as above in steps 101–103, and then stored at an appropriate temperature as in step 104. At a later date when the appropriate recipient for the stored donor organ becomes available, it can be thawed and transplanted as in step 105. One embodiment of the invention utilizes a washing solution that is followed by a preservation solution to thaw the stored organ in preparation for the transplantation procedure.

Figure 2A:
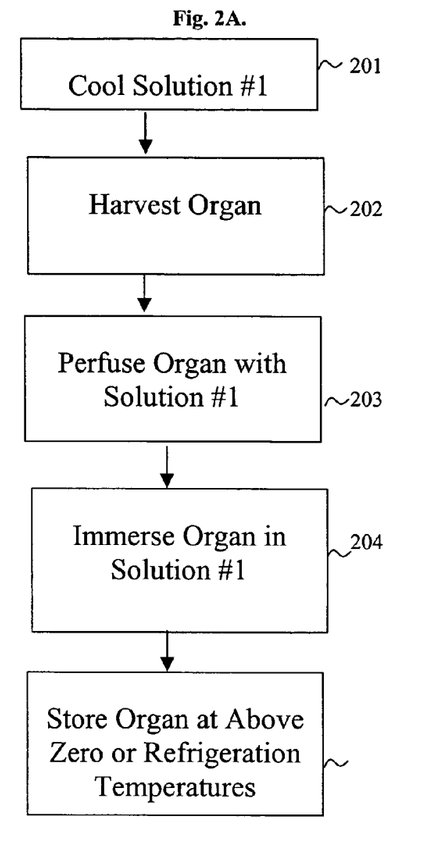
FIG. 2 is a flowchart illustrating the operation of two embodiments of the invention wherein a donor organ can be stored at refrigeration temperatures as in FIG. 2A or at freezing temperatures as in FIG. 2B.

FIG. 2 provides two flowcharts each illustrating an embodiment whereby a donor organ can be stored at a different temperature. The flowchart in FIG. 2A illustrates a series of steps in accordance with this aspect of the invention for preserving a donor organ at refrigeration temperatures, which are defined herein as between approximately 0° C. and 6° C. Step 201 involves the cooling to 2° and 4° C. of Solution #1, which is a refrigeration preservation solution provided in accordance with another aspect of the invention. This mixture can have a pH of 7.0 to 7.5, and can contain a variety of ingredients such as a hydrophilic polymer, a saccharide, a vinyl polymer, a calcium ion flux inhibitor, a dihydrofolate reductase inhibitor, a bacteriostatic, antibacterial agent, a nucleoside, amino acids, salts, an energy source for the citric acid cycle, a steroid analogue, a membrane stabilizer, and a diuretic. Step 202 represents the harvesting of a donor organ. After cooling and harvesting, the organ is perfused with Solution #1 as shown in step 203. Following perfusion, the organ is immersed in Solution #1 as shown in step 204 and stored at 2° and 4° C. for 36 hours before transplantation, as shown in step 205.

Figure 2B:
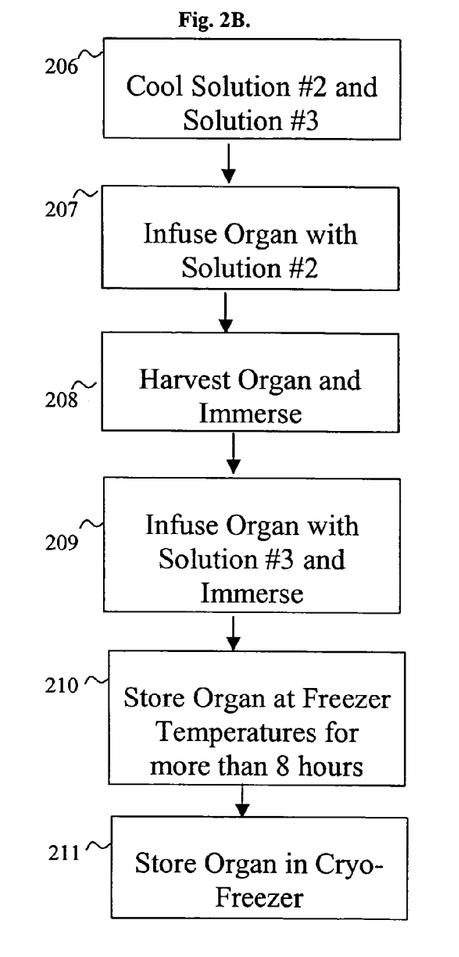

The flowchart in FIG. 2B describes yet another embodiment of the invention for storage of donor organs at freezer temperatures, defined herein as between approximately −1° and −80° C. Step 206 represents the cooling of both Solution #2, a loading pre-freezer preservation solution, and Solution #3, a cryopreservation solution. Solution #2 may contain a hydrophilic polymer, a saccharide, a vinyl polymer, a calcium ion flux inhibitor, a dihydrofolate reductase inhibitor, a bacteriostatic, antibacterial agent, a nucleoside, amino acids, salts, an energy source for the citric acid cycle, a steroid analogue, a membrane stabilizer, and a diuretic. Solution #3 contains the same ingredients as Solution #2 but also contains a number of cryopreservatives, including glycerol, propanediol, an alcohol and a cryoprotectant agent. A quantity of Solution #2 is cooled to a temperature between 2° and 4° C. In addition, a quantity of Solution #2 and #3 is further cooled to a temperature between 0° and 2° C. As represented by step 207, a needle such as a 27 g needle is then inserted into the isolated arterial system of the organ before removal from the donor, and Solution #2 cooled at 2° to 4° C., is infused via the needle for approximately 1 minute. In step 208 the organ is removed from the donor and immersed in Solution #2 which is cooled to 0° and 2° C., and maintained at that temperature for 30 minutes. In step 209, the organ is kept at 0° to 2° C. and a quantity of Solution #3 cooled to 0° and 2° C. is gradually infused via the needle. Then the donor organ is immersed in Solution #3 cooled to 0° and 2° C. for 30 minutes. Following this incubation, the donor organ is stored in Solution #3 at a temperature below 0° C. as in step 210.

In another embodiment of the invention as shown in FIG. 2B, an additional step can be provided that follows step 210. The donor organ can be then transferred to cryofreezer temperatures, which can be defined as about −80° C. or lower as shown in step 211. However, it is preferable for the donor organ to be stored at −20° C. for at least 8 hours before it is transferred to lower temperatures such as −80° C.

Figure 3A:
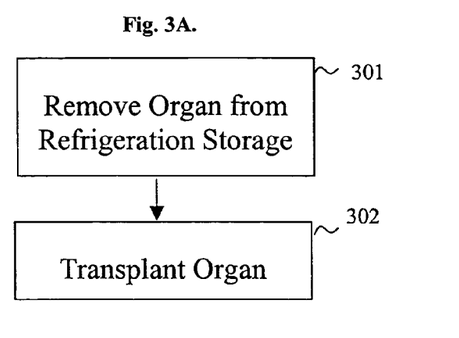
FIG. 3 is a flowchart illustrating the operation of different embodiments of the invention wherein a preserved donor organ can either be removed from cold storage or refrigeration temperatures and transplanted as in FIG. 3A, or thawed from freezer temperatures as in FIG. 3B and transplanted.
Figure 3B:
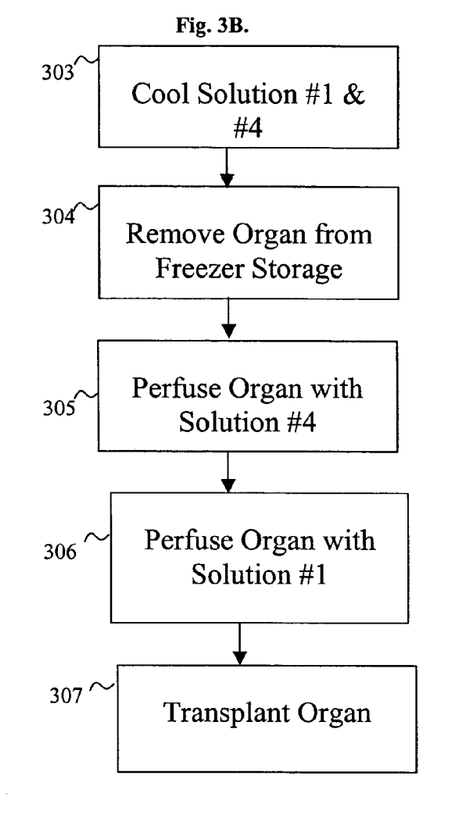

FIGS. 3A–B provide flowcharts that illustrate the methodology and operation of alternative embodiments of the invention. A preserved organ can either be removed from refrigeration temperatures and transplanted as shown in FIG. 3A. In FIG. 3A, the donor organ is removed directly from storage at refrigeration temperatures in step 301 and transplanted into a suitable recipient in step 302. Alternatively, an organ can be thawed from freezer temperatures, and subsequently transplanted as indicated in FIG. 3B. FIG. 3B provides the steps for transplantation of a donor organ stored at freezer temperatures. Step 303 illustrates the first requirement of cooling Solution #1 and Solution #4 to a temperature between 2° C. and 4° C. The organ is then removed from freezer temperature storage in step 304 and perfused with cooled Solution #4 as shown in step 305. Solution #4 is a washing solution containing a hydrophilic polymer, a saccharide, a vinyl polymer, a calcium ion flux inhibitor, a dihydrofolate reductase inhibitor, a bacteriostatic, antibacterial agent, a nucleoside, amino acids, salts, an energy source for the citric acid cycle, a steroid analogue, a membrane stabilizer, and a diuretic. Following step 305, the organ is perfused with cooled Solution #1 according to step 306. Step 307 represents the transplantation of the organ into a suitable recipient.

An alternate embodiment of the invention provides suitable solutions and methods for organ storage at cryofreezer temperatures. The steps described in FIG. 3B can be first preceded by an additional step. A preserved donor organ can be removed from storage at cryofreezer temperatures and placed at freezer temperatures for 8 hours or more. After this period, the donor organ may be transplanted following steps 304–308 in FIG. 3B.

Solutions used for Preservation Storage and Transplantation

One of the most widely used solutions in organ preservation and storage is known as University of Wisconsin (UW) solution or Viaspan, which is manufactured by DuPont. However, preservation of donor organs using Viaspan is generally limited to a 36-hour period in kidneys before the organs begin to deteriorate. The solutions described herein may allow for significantly longer storage periods.

A variety of organ preservation and storage solutions are provided herein in accordance with invention. These preservation solutions may contain one or more of the following ingredients: a large molecule hydrophilic polymer used for cellular protection of the organ, agents for reducing interstitial edema or fluid buildup inside cells, an energy source for cellular functions, agents for maintaining cellular ion concentrations including a variety of salts, and series of one or more amino acids that can help prevent proteolysis and to scavenge free radicals as antioxidants. Other solution additives may include cell membrane stabilizers and anti-inflammatory agents.

Figure 4:
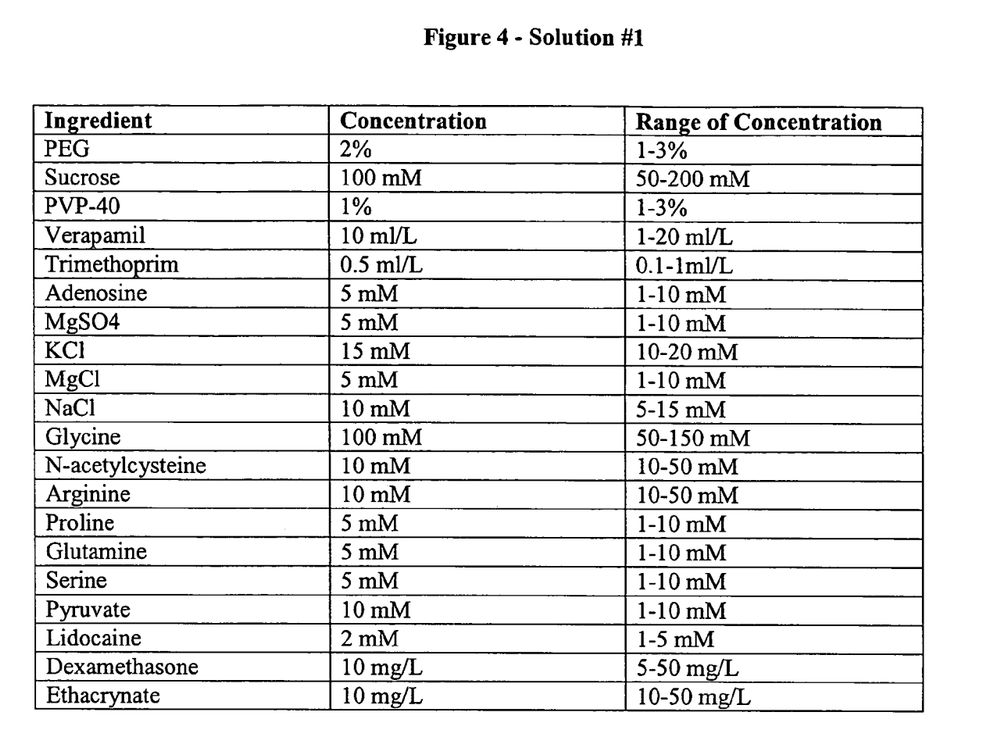
FIG. 4 is a table that lists the composition of a refrigeration preservation solution, Solution #1, provided in accordance with another aspect of the invention. In addition, a range of concentrations is provided to illustrate some other variations of the ingredients that may be used for Solution #1.

The table in FIG. 4 lists a solution provided in accordance with another aspect of the invention, Solution #1, a refrigeration preservation solution. In addition, a range of concentrations is provided to illustrate some other embodiments that may be used for Solution #1. Solution #1 includes for example polyethylene glycol (PEG), which is a large molecular hydrophilic polymer used to protect the cells of the donor organ by preventing the passage of extracellular solutes through an organ cells' membranes. The PEG from Sigma-Aldrich, product P2263, may be preferably used but any comparable or equivalent chemical can be used in place of PEG. Polyvinylpyrrolidone or PVP-40 is a large molecular vinyl polymer. PVP-40 can be used in a manner similar to PEG. PVP-40 protects donor organ cells from an influx of excess solutes. Its large size generally serves to prevent solute entry. A preferable form of PVP-40 from Sigma-Aldrich, product P0930, or any other comparable chemical may be used. Sucrose is a disaccharide and as a large molecule also functions to prevent solute entry into the cells of the donor organ. It also helps reduce the amount of interstitial edema, or fluid buildup, inside the cells. Another ingredient of Solution #1 is verapamil, which is a calcium ion influx inhibitor for preventing the entry of extracellular calcium ions into the donor organ cells. Verapamil may protect donor organ cells by preventing an elevation of intracellular calcium concentration, which can limit the activation of inflammatory pathways after long storage preservation periods. Moreover, it has been observed that verapamil can also provide protection by down-regulating infiltration of neutrophils or other immune response elements. Lopez-Neblina F, et al. "Mechanism of protection of verapamil by preventing neutrophil infiltration in the ischemic rat kidney" J. Surg. Res. (March 1996) Volume 61(2), pages 469–72. The trimethoprim ingredient consists of a solution containing 16 mg/ml of trimethoprim and 80 mg/ml of sulfamethoxazole. Both are antibacterial agents used to prevent infection of the donor organ. Adenosine is a nucleoside that plays a role in metabolic energy transfers. It serves as another energy source in Solution #1. Each listed salt $MgSO_4$, NaCl, KCl, MgCl can be present in Solution #1 and used to preserve the proper intracellular concentration of ions. Proper ionic gradients across the donor organ cell membranes are maintained through the use of these salts. The amino acids, glycine, arginine, serine, proline, glutamine and N-acetylcysteine are used to prevent proteoloysis and to scavenge free radicals as antioxidants. In addition, acetylcysteine itself enhances the production of the enzyme glutathione, which is a powerful antioxidant. Pyruvate is present in Solution #2 as the primary energy source for the donor organ cells. It is the main input into the citric acid cycle, which allows cells to utilize oxygen for cellular respiration and the generation of energy. Lidocaine is a local anesthetic used to stabilize cell membranes and to some extent, to prevent ischemic and reperfusion damage, as well as subsequent swelling of the donor organ cells. Dexamethasone is a steroid that functions as an anti-inflammatory agent. It helps reduce endothelial cell swelling. Ethacrynate is a diuretic that serves to reduce interstitial edema or fluid buildup.

Figure 5:
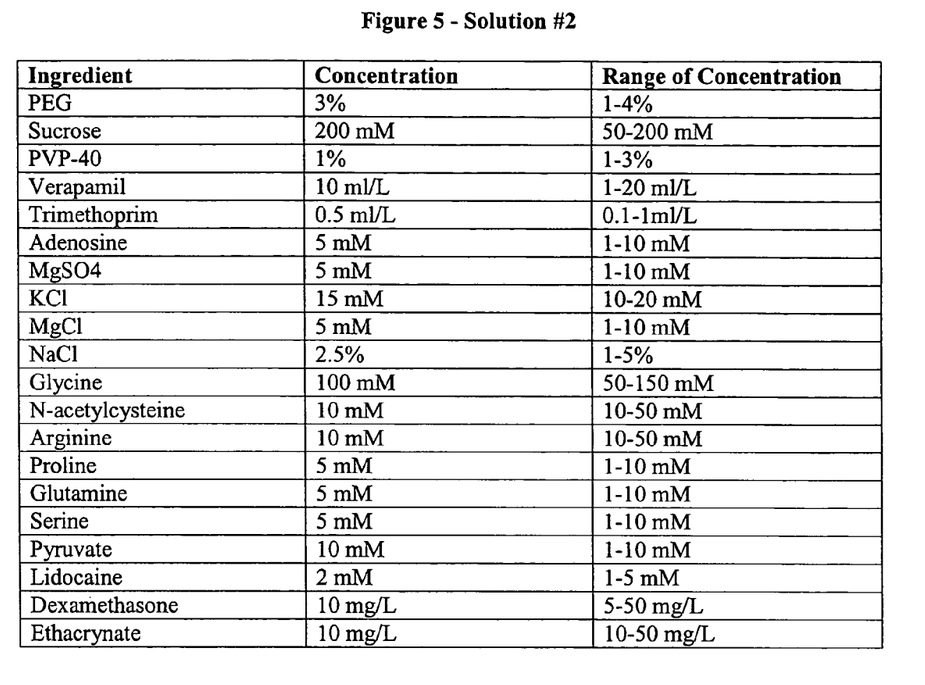
FIG. 5 is a table that lists the components of the loading pre-freezer preservation solution, Solution #2, which may be used before treatment with a cryopreservation solution. In addition, a range of concentrations for these components is provided to illustrate some other alternatives of Solution #2.

FIG. 5 provides a table illustrating another embodiment of the invention, Solution #2. Solution #2 is a loading pre-freezer preservation solution that includes an illustrated list of ingredients that vary within a range of concentrations. This solution contains a higher concentration of polyethylene glycol (PEG) than Solution #1 because the storage conditions will be lower than 0° C. The additional PEG may provide additional cryoprotection at these temperatures. In addition, the large molecular size of PEG, sucrose and PVP-40 provide protection against the influx of extracellular solutes into the donor organ cells, and also produce a slight dehydration that allows better cryoprotection. Verapamil serves as a calcium ion influx inhibitor, just as it did in Solution #1. Verapamil is a phenylalkylamine calcium channel blocker. There are a number of classes of calcium channel blockers that might be used in place of verapamil. For example, diltiazem (a benzothiazepine), nicardipine, nifedipine, or nimodipine (all dihydropyridines), bepridil (a diarylaminopropylamine ether) and mibefradil (a benzimidazole-substituted tetraline) may all serve the same function in Solutions #1 –#4. Trimethoprim is a dihydrofolate reductase inhibitor and is used as a bactericidal to stop folic acid production in bacteria. Other bactericidals may be used in its place, such as those in the following classes: penicillins, cephalosporins, and aminoglycosides. Sulfamethoxazole serves as an anti-microbial agent just as it did in Solution #1. This agent is one of a group of drugs called sulfonamides, which prevent bacterial growth in the body. Other members of this group may be substituted for sulfamethoxazole in Solutions #1–4, such as sulfadiazine. Adenosine and the salts $MgSO_4$, NaCl, KCl, MgCl, all serve the same function as they did in Solution #1 but the higher concentration of NaCl causes a slight dehydration that is protective in nature because it decreases the amount of water in the cells and by doing so limits the formation of ice crystals. The amino acids, glycine, arginine, serine, proline, glutamine and N-acetylcysteine act as anti-proteolytic agents and/or anti-oxidants. Pyruvate inputs into the citric acid cycle, lidocaine stabilizes the donor organ cell membranes, dexamethasone provides anti-inflammatory protection and ethacrynate helps to reduce interstitial edema.

Figure 6:
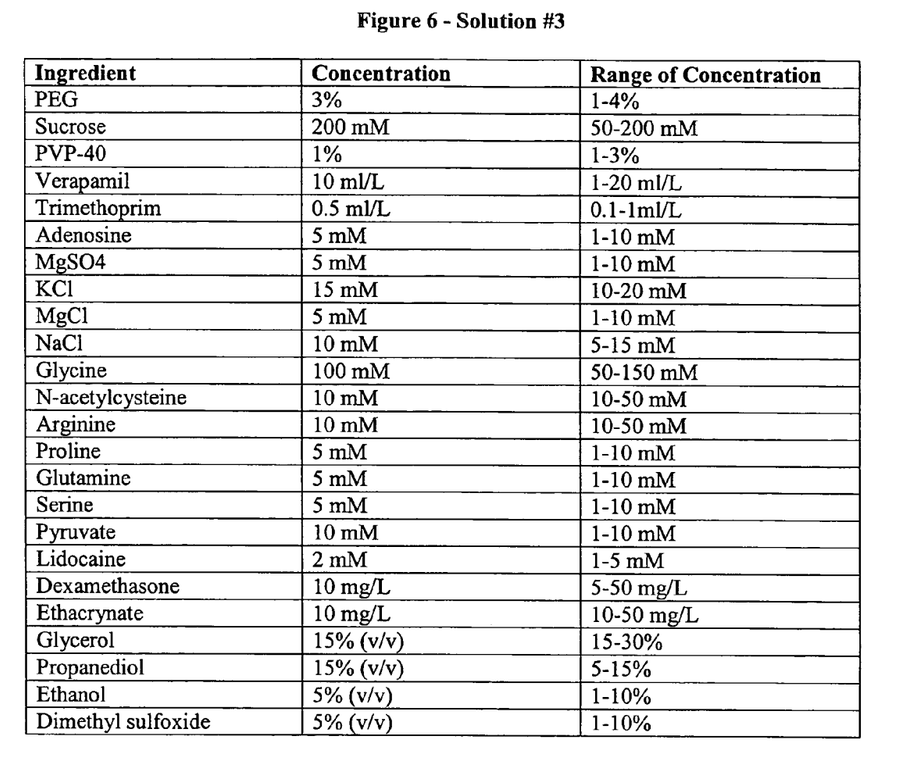
FIG. 6 is a table that lists another embodiment of the invention that provides a cryopreservation solution, Solution #3. In addition, a range of concentrations is provided to illustrate some other variations of solution ingredients that may be used for Solution #3.

FIG. 6 is a table that lists another embodiment of the invention, Solution #3, which is a cryopreservation solution. A range of concentrations is provided to illustrate some other variations of Solution #3 that can be used in accordance with the invention. As in Solution #2, the PEG concentration can be higher to cope with the lower temperatures at which the organ will be stored. PEG, sucrose and PVP-40 play a similar role a cryopreservants and their large molecular size prevents the entry of extracellular solutes. Other disaccharides besides sucrose may be substituted, such as lactose, maltose, isomaltose, or cellobiose. In addition, PVP-40 may be substituted with alternate macromolecules, such as the complex colloidal Dextran-40 or gelatin. Trimethoprim and sulfamethoxazole are added as anti-microbial agents, adenosine and pyruvate are added as energy sources, and the salts are added to preserve safe ionic gradients across the donor organ cell membranes. As in Solutions #1 and #2, the amino acids, glycine, arginine, serine, proline, glutamine and N-acetylcysteine are added to prohibit proteolysis of cellular proteins. These amino acids, particularly serine and proline, may be substituted with other amino acids of a similar function, such as alanine, histidine, leucine, methionine, phenylalanine and tryptophan. The members of the latter group all have anti-proteolytic activity. As in Solutions #1 and #2, lidocaine serves to stabilize cell membranes, dexamethasone prevents inflammation of the donor organ and ethacrynate reduces interstitial edema and the initial induction of diuresis or urine excretion. Solution #3 is a cryopreservation solution and can therefore contain ingredients not found in Solutions #1 and #2. For example, a variety of anti-freeze components can be included such as four different types in Solution #3. Two are glycerol and ethanol, both alcohols with a low freezing point, which allows them to prevent the organ from freezing at temperatures below freezing. Propanediol, another anti-freeze agent, is a third ingredient and dimethyl sulfoxide (DMSO) is the fourth. Besides being an organic solvent that keeps all the ingredients in solution, DMSO is a well-known cryoprotective agent that lowers the freezing point and allows a slow cooling rate. It is effective at preventing donor organ cells from freezing at subzero temperatures.

It is important to note that the NaCl concentration is generally higher in Solution #2 than in Solutions #3 and #4 because the organ is being dehydrated slightly. This removal of water from the cell will reduce the likelihood that ice crystals will be formed during the freezing process of the organ. The DMSO in Solution #3 also plays a role by replacing the lost water from the cell. As DMSO has a lower freezing point, the cell will be less likely to form ice crystals.

Figure 7:
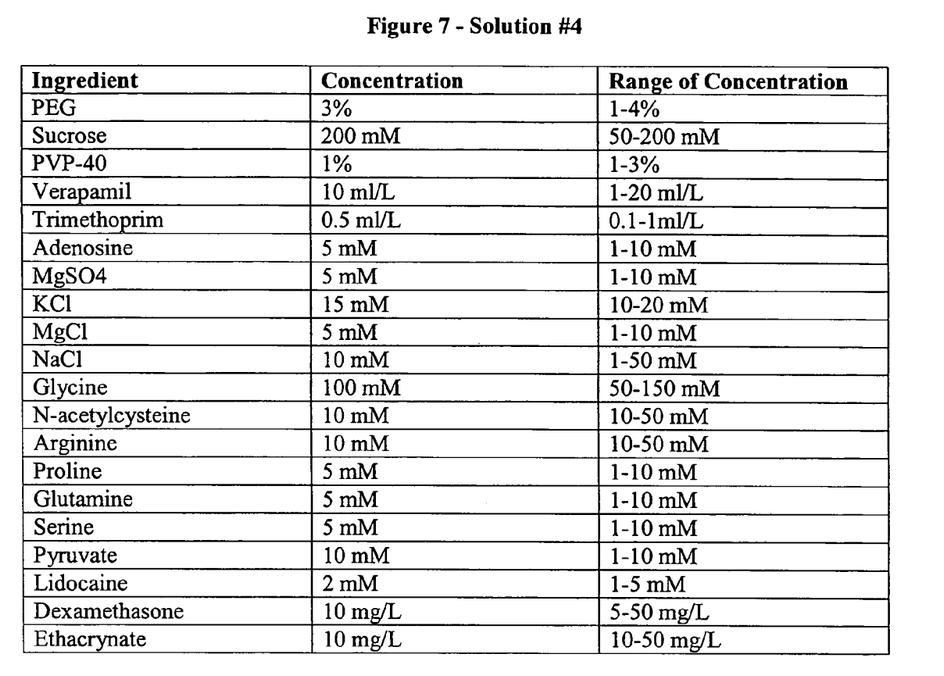
FIG. 7 is a table that lists the composition of a washing solution, Solution #4. In addition, a range of ingredient concentrations is provided to illustrate some other variations of Solution #4 that may be used in accordance with this aspect of the invention.

FIG. 7 is a table that lists another embodiment of the invention, Solution #4, which is a washing solution. In addition, a range of concentrations is provided to illustrate some other variations of Solution #4 provided herein. The washing solution substantially contains the same macromolecules, PEG, PVP-40 and sucrose to help prevent an influx of extracellular solutes. Verapamil is present to block calcium ion entry, trimethoprim and sulfamethoxazole are present as anti-microbial agents, pyruvate and adenosine are present as energy sources, the same salts preserve proper ionic gradients, and lidocaine stabilizes the cell membranes. The adrenal cortical steroid, dexamethasone is included to stop inflammation of the organ. However, other such steroids may be substituted for dexamethasone, such as hydrocortisone, aldactone, or aristocort. Ethacrynate is included in Solution #4 as a diuretic to reduce interstitial edema.

Solution #4, the washing solution, generally contains the same ingredients as found in Solutions #1 and #2, except the concentration of NaCl is typically lower than in Solution #1. This allows Solution #4 to wash out the cryosolution, Solution #3, and rehydrate the cell. The DMSO from Solution #3 that had replace water in the cell prior to freezing is washed out and water is added back as the temperature of the stored organ is restored to normal.

It is important to note that the concentrations and the ranges of concentrations of each ingredient of Solutions #1–#4 are relatively low compared to other organ preservation/storage solutions currently available, such as Viaspan. Viaspan contains ingredients in higher concentrations than the solutions described herein. Higher ingredient concentration however generally increases the toxicity of the solution to the donor organ.

Kit for Organ Preservation, Storage and Transplantation

In accordance with yet another aspect of the invention, each of the Solutions #1, #2, #3 and #4 described herein can be stored in separate containers within a single package or a kit. Such kits may be marketed to entities engaged in the business or activities of harvesting, storing, preserving and/or transplanting donor organs. These kits may include instructions for methods of organ preparation and storage as described elsewhere herein. In accordance with an aspect of the invention, various types of mammalian organs can be treated and prepared for storage over extended periods of time. While experiments were conducted in the following examples with rat kidneys, the invention here can be applied to human subjects or other mammals and their respective organs.

Organ Storage at Cold Storage or at Refrigerator Temperatures

EXAMPLE 1

Donor rat kidneys were harvested by usual methods and perfused with Solution #1 (described below), comprised of ingredients listed in the table below. This solution is a mixture designed to reduce interstitial edema and endothelial swelling, contains antioxidants and anti-proteolytic amino acids, and preserves proper intracellular concentrations of ions including magnesium, sodium, and potassium. This solution is comprised of macromolecules, impermeable molecules, amino acids, energy sources that support the Krebs cycle, and salts. The pH of this solution is about 7.3+/−0.1.

The kidneys that were perfused with Solution #1 were stored in a refrigerator at about 2° to 4° C. for 36 hours and then transplanted into anephric rats using a published method. The transplanted kidneys were observed to quickly turned pink with fresh blood and immediately began producing urine.

In contrast, donor kidneys perfused with UW solution and stored for 36 hours in the refrigerator did not turn as bright with blood nor did they make appropriate amounts of urine after transplantation.

Organs perfused or stored in a solution such as this Solution #1 or equivalent solution can be stored for extended periods and recover and function rapidly after transplantation. Specifically, kidneys can be stored for 36 hours, 40 hours, 48 hours, 50 hours, or longer and then transplanted and are viable and they function.

Organ Storage at Sub-Zero Temperatures (below 0° C.)

Two solutions are used in sequence to perfuse or wash organs in preparation for sub-zero storage (Solution #2 and Solution #3 described below). After storage at sub-zero temperature, Solution #3 is washed out with Solution #4 (described below) followed by washing with Solution #1, and the organ is transplanted. These solutions #2, #3, and #4 are similar to Solution #1 with some modifications for use in cryopreservation (storage at sub-zero temperatures). Solution #3 (cryosolution) contains cryoprotectants. All solutions are cold at about 2 to 4° C. when used for perfusing or washing organs.

EXAMPLE 1

The donor rat kidneys were perfused for 30 minutes at 2° to 4° C. with Solution #2 which is the same as Solution #1 except that sodium chloride is at 2.5% and amounts of PEG and sucrose are increased. Then the donor kidneys were perfused at 2° to 4° C. for 30 minutes with Solution #3 (cryopreservation solution). The kidneys were placed into a refrigerator's freezer at about −20° C. Kidneys were stored for days, but could be stored for much longer periods or weeks or months.

The kidneys did not freeze because of the use of the perfusion solutions and the system utilized as indicated above.

After removing the kidneys from the freezer, the kidneys were perfused with a washing solution (Solution #4), which is identical to Solution #2 except that the amount of NaCl is 10 mM. Finally, kidneys were perfused for 30 minutes with Solution #1 and transplanted. The transplanted kidneys were observed to turn pink in color as they were reperfused with blood and immediately produced urine.

The solutions used in this example are comprised as listed in the tables below.

By following the method stated above and using the invented solutions described, or essentially equivalent solutions, organs can be stored at sub-zero temperatures for extended periods of time of days, weeks, or months, until used for transplantation by following the stated method of this invention.

Solutions listed below are all at a pH of about 7.3+/−0.1 in a phosphate buffer comprised of 950 ml water, 10 ml 1 M monobasic phosphate, and 40 ml 1 M dibasic phosphate.

EXAMPLE 2

The following is a description of a procedure in accordance with the invention for organ storage of four rat kidneys at temperatures as low as about −80° C. The same solutions described herein may be applied for storage at temperatures generally in this range.

Each of the kidneys can be dissected in a standard manner isolating the renal flow with silk. The venous drainage is opened which may be accomplished usually by sectioning the renal vein. A 27 g needle may be inserted in the isolated arterial system so flushing of the kidney can start immediately. It is desirable to avoid air circulation or the introduction of air bubbles into the system during this process. An infusion with 1 ml of volume of the loading hypertonic solution (Solutions #2) may be performed in about 1 minute at 2 to 4° C. Then the organ is removed and immediately immersed in the same solution at 0 to 2° C., and is maintained at this temperature in the loading solution for 30 minutes. Then the infusion of 10 ml of the subzero solution (anti-freeze Solution #3) is initiated at 0.300 ml per minute, and the kidney is maintained at 0 to 2° C. during this infusion. The graft immersed in the antifreeze solution is subsequently placed in the freezer at −20° C. for 12 hours, and then placed in the cryo-freezer at −80° C. for cryo-preservation.

To warm up the organ after its storage at −80° C. for cryo-preservation, it is initially placed in a −20° C. surrounding for 12 hours (regular freezer). Afterwards it is placed at a 0 to 2° C. environment, and then 10 ml of the washing solution (Solution #4) is introduced at 0.300 ml per minute. The kidney is maintained at 0 to 2° C. during this infusion. Subsequently the graft is placed in a refrigerator at 2 to 4° C. for at least one hour. Each of the kidneys were then transplanted in a customary fashion and then allowed circulation of blood. The Reperfusion Damage Index was measured during the first 15 minutes. The graft was removed at 60 minutes of reperfusion and placed in buffered formal in 10% for histology (H&E) and pictures taken at 600×. The histology yielded positive results with intact glomeruli and the cellular structure in the kidneys were generally maintained following organ storage at –80° C. in accordance with the invention herein.

As evidenced by the examples mentioned above, the methods and solutions herein provide organ storage at temperatures as low as –20° C. or even lower at about –80° C. These techniques may be applied to other mammalian organs including human kidneys.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of preserving at freezer temperatures mammalian donor organs for transplantation comprising:
   cooling a loading, pre-freezer preservation solution at least containing polyvinylpyrrolidone -40, a calcium channel blocker, a nucleoside, potassium chloride, polyethylene glycol, at least one amino acid and a steroid to a temperature between 2° C. and 4° C.;
   cooling a quantity of the loading, prefreezer preservation solution to a temperature between 0° C. and 2° C.;
   cooling a cryopreservation solution at least containing polyvinylpyrrolidone -40, a calcium channel blocker, a nucleoside, potassium chloride, polyethylene glycol, at least one amino acid, a steroid, glycerol, propanediol, an alcohol and an alkyl sulfoxide to a temperature between 0° C. and 2° C.;
   inserting a needle into the isolated arterial system of the donor organ before removal from a donor;
   infusing the donor organ with the loading, pre-freezer preservation solution cooled to a temperature between 2° C. and 4° C. through the needle;
   harvesting the donor organ;
   immersing for 10 minutes or longer the donor organ in the loading, pre-freezer preservation solution cooled to a temperature between 0° to 2° C.;
   infusing the donor organ with the cryopreservation solution cooled to a temperature between 0° to 2° C. through the needle in a gradual manner;
   immersing for 10 minutes or longer the donor organ in the cryopreservation solution cooled to a temperature of 0° C. to 2° C.;
   storing the donor organ in the cryopreservation solution at a temperature below 0° C.

2. The method of claim 1 including the further steps of storing the donor organ at a temperature below 0° C. for 8 hours or more; and
   transferring the donor organ to a cryofreezer temperature of about –80° C.

3. The method of claim 1 wherein the calcium channel blocker is verapamil.

4. The method of claim 1 wherein the nucleoside is adenosine.

5. The method of claim 1 wherein the amino acid or amino acids are selected from a group consisting of N-acetylcysteine, glycine, arginine, proline, glutamate, serine, alanine, histidine, leucine, methionine, phenylalanine and tryptophan.

6. The method of claim 1 wherein the steroid is dexamethasone.

7. The method of claim 1 wherein the loading pre-freezer preservation solution and the cryopreservation solution each have a pH between 7.0 and 7.5.

8. The method of claim 1 wherein the donor organ is a mammalian heart, liver, kidney, or pancreas.

9. A method of transplanting a donor organ that has been preserved according to claim 1, comprising
   cooling a washing solution at least containing (PVP-40), a calcium channel blocker, a nucleoside, potassium chloride, polyethylene glycol, at least one amino acid, a steroid, glycerol, propanediol, an alcohol and an alkyl sulfoxide to a temperature between 2° and 4° C.
   cooling a refrigeration preservation solution to a temperature between 2° and 4° C.;
   removing the donor organ from storage at a temperature below 0° C.;
   perfusing the donor organ with the washing solution cooled at 2° to 4° C.;
   perfusing the donor organ with the refrigeration preservation solution cooled at 2° and 4° C.; and
   transplanting the donor organ.

10. The method of claim 9 wherein the first step of cooling of a washing solution is preceded by the transfer of a donor organ stored at cryofreezer temperatures to storage at freezer temperatures for a period of 8 hours or more.

11. The method of claim 9 wherein the calcium channel blocker is verapamil.

12. The method of claim 9 wherein the nucleoside is adenosine.

13. The method of claim 9 wherein the amino acid or amino acids are selected from a group consisting of N-acetylcysteine, glycine, arginine, proline, glutamate, serine, alanine, histidine, leucine, methionine, phenylalanine and tryptophan.

14. The method of claim 9 wherein the steroid is dexamethasone.

15. The method of claim 9 wherein the washing solution has a pH between 7.0 and 7.5.

* * * * *